(12) United States Patent
Huter et al.

(10) Patent No.: US 7,244,267 B2
(45) Date of Patent: *Jul. 17, 2007

(54) FILTER DEVICE FOR EMBOLIC PROTECTION SYSTEMS

(75) Inventors: Benjamin C. Huter, Murrieta, CA (US); John E. Papp, Temecula, CA (US); Anuja Patel, San Jose, CA (US); John D. Whitfield, Temedula, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 409 days.

This patent is subject to a terminal disclaimer.

(21) Appl. No.: 10/465,332

(22) Filed: Jun. 19, 2003

(65) Prior Publication Data

US 2003/0225435 A1 Dec. 4, 2003

Related U.S. Application Data

(63) Continuation of application No. 09/919,503, filed on Jul. 31, 2001, now Pat. No. 6,599,307, which is a continuation-in-part of application No. 09/896,142, filed on Jun. 29, 2001, now Pat. No. 6,656,202.

(51) Int. Cl.
*A61M 29/00* (2006.01)

(52) U.S. Cl. .................................... 606/200

(58) Field of Classification Search ............... 606/114, 606/113, 127, 159, 194, 200; 604/104–109, 604/171–172, 265
See application file for complete search history.

(56) References Cited

U.S. PATENT DOCUMENTS 3,952,747 A  4/1976  Kimmell, Jr.
4,452,908 A  6/1984  Ball et al.
4,494,531 A  1/1985  Gianturco
4,612,931 A  9/1986  Dormia (Continued)

FOREIGN PATENT DOCUMENTS

EP  0427429 A3  9/1991

(Continued)

OTHER PUBLICATIONS

Dilitation of the Carotid Artery By A Temporary Carotid Filter By A. Beck, St. Milic, A.M. Spagnoli, Nov. - Dec. Issue of OPLITAI, An International Journal on Military Medicine and Health Emergencies, pp. 67-74.

*Primary Examiner*—Michael J. Hayes
*Assistant Examiner*—Victor Nguyen
(74) *Attorney, Agent, or Firm*—Fulwider Patton LLP

(57) ABSTRACT

A system for enabling the insertion and removal of an embolic protection device, for capturing and retaining embolic debris which may be created during the performance of a therapeutic interventional procedure in a stenosed or occluded region of a blood vessel. The system, in an embodiment thereof, enables the device to be snap-fitted so as to engage the distal end of a guide wire, to provide a reference for positioning the device at a location distal to the interventional procedure site, and to enable an end of the device to be in tension, enabling a portion of the device to be in tension and another portion to be in compression, so as to assist in bending thereof in tortuous vasculature.

19 Claims, 2 Drawing Sheets

U.S. PATENT DOCUMENTS

| | | |
|---|---|---|
| 4,619,246 A | 10/1986 | Molgaard-Nielsen et al. |
| 4,643,184 A | 2/1987 | Mobin-Uddin |
| 4,650,466 A | 3/1987 | Luther |
| 4,662,885 A | 5/1987 | DiPisa, Jr. |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,794,928 A | 1/1989 | Kletschka |
| 4,832,055 A | 5/1989 | Palestrant |
| 4,873,978 A | 10/1989 | Ginsburg |
| 4,921,478 A | 5/1990 | Solano et al. |
| 4,921,484 A | 5/1990 | Hillstead |
| 4,969,891 A | 11/1990 | Gewertz |
| 4,990,156 A | 2/1991 | Lefebvre |
| 4,997,435 A | 3/1991 | Demeter |
| 4,998,539 A | 3/1991 | Delsanti |
| 5,053,008 A | 10/1991 | Bajaj |
| 5,064,428 A | 11/1991 | Cope et al. |
| 5,071,407 A | 12/1991 | Termin et al. |
| 5,092,839 A | 3/1992 | Kipperman |
| 5,100,423 A | 3/1992 | Fearnot |
| 5,100,425 A | 3/1992 | Fischell et al. |
| 5,102,415 A | 4/1992 | Guenther et al. |
| 5,108,419 A | 4/1992 | Reger et al. |
| 5,152,777 A | 10/1992 | Goldberg et al. |
| 5,158,548 A | 10/1992 | Lau et al. |
| 5,160,342 A | 11/1992 | Reger et al. |
| 5,192,286 A | 3/1993 | Phan et al. |
| 5,201,757 A * | 4/1993 | Heyn et al. .................. 606/198 |
| 5,324,304 A | 6/1994 | Rasmussen |
| 5,329,942 A | 7/1994 | Gunther et al. |
| 5,330,482 A | 7/1994 | Gibbs et al. |
| 5,350,398 A | 9/1994 | Pavcnik et al. |
| 5,370,657 A | 12/1994 | Irie |
| 5,375,612 A | 12/1994 | Cottenceau et al. |
| 5,383,887 A | 1/1995 | Nadal |
| 5,421,832 A | 6/1995 | Lefebvre |
| 5,490,859 A | 2/1996 | Mische et al. |
| 5,496,277 A | 3/1996 | Termin et al. |
| 5,496,330 A | 3/1996 | Bates et al. |
| 5,501,694 A | 3/1996 | Ressemann et al. |
| 5,549,626 A | 8/1996 | Miller et al. |
| 5,601,595 A | 2/1997 | Smith |
| 5,626,605 A | 5/1997 | Irie et al. |
| 5,634,942 A | 6/1997 | Chevillon et al. |
| 5,649,953 A | 7/1997 | Lefebvre |
| 5,658,296 A | 8/1997 | Bates et al. |
| 5,662,671 A | 9/1997 | Barbut et al. |
| 5,669,933 A | 9/1997 | Simon et al. |
| 5,681,347 A | 10/1997 | Cathcart et al. |
| 5,695,518 A | 12/1997 | Laerum |
| 5,695,519 A | 12/1997 | Summers et al. |
| 5,720,764 A | 2/1998 | Naderlinger |
| 5,725,550 A | 3/1998 | Nadal |
| 5,746,767 A | 5/1998 | Smith |
| 5,755,790 A | 5/1998 | Chevillon et al. |
| 5,769,816 A | 6/1998 | Barbut et al. |
| 5,772,674 A | 6/1998 | Nakhjavan |
| 5,776,162 A | 7/1998 | Kleshinski |
| 5,779,716 A | 7/1998 | Cano et al. |
| 5,792,145 A | 8/1998 | Bates et al. |
| 5,792,156 A | 8/1998 | Perouse |
| 5,792,157 A | 8/1998 | Mische et al. |
| 5,795,322 A | 8/1998 | Boudewijn |
| 5,800,457 A | 9/1998 | Gelbfish |
| 5,800,525 A | 9/1998 | Bachinski et al. |
| 5,810,874 A | 9/1998 | Lefebvre |
| 5,814,064 A | 9/1998 | Daniel et al. |
| 5,827,324 A | 10/1998 | Cassell et al. |
| 5,833,650 A | 11/1998 | Imran |
| 5,836,868 A | 11/1998 | Ressemann et al. |
| 5,846,251 A | 12/1998 | Hart |
| 5,846,260 A | 12/1998 | Maas |
| 5,848,964 A | 12/1998 | Samuels |
| 5,868,708 A | 2/1999 | Hart et al. |
| 5,876,367 A | 3/1999 | Kaganov et al. |
| 5,897,567 A | 4/1999 | Ressemann et al. |
| 5,910,154 A | 6/1999 | Tsugita et al. |
| 5,911,734 A | 6/1999 | Tsugita et al. |
| 5,935,139 A | 8/1999 | Bates |
| 5,941,869 A | 8/1999 | Patterson et al. |
| 5,941,896 A | 8/1999 | Kerr |
| 5,944,728 A | 8/1999 | Bates |
| 5,954,745 A | 9/1999 | Gertler et al. |
| 5,968,071 A | 10/1999 | Chevillon et al. |
| 5,976,172 A | 11/1999 | Homsma et al. |
| 5,980,555 A | 11/1999 | Barbut et al. |
| 5,989,281 A | 11/1999 | Barbut et al. |
| 6,001,118 A | 12/1999 | Daniel et al. |
| 6,007,557 A | 12/1999 | Ambrisco et al. |
| 6,013,093 A | 1/2000 | Nott et al. |
| 6,022,336 A | 2/2000 | Zadno-Azizi et al. |
| 6,027,520 A | 2/2000 | Tsugita et al. |
| 6,042,598 A | 3/2000 | Tsugita et al. |
| 6,051,015 A | 4/2000 | Maahs |
| 6,053,932 A | 4/2000 | Daniel et al. |
| 6,059,814 A | 5/2000 | Ladd |
| 6,066,158 A | 5/2000 | Engelson et al. |
| 6,074,357 A | 6/2000 | Kaganov et al. |
| 6,086,605 A | 7/2000 | Barbut et al. |
| 6,090,097 A | 7/2000 | Barbut et al. |
| 6,096,053 A | 8/2000 | Bates |
| 6,099,534 A | 8/2000 | Bates et al. |
| 6,099,549 A | 8/2000 | Bosma et al. |
| 6,117,154 A | 9/2000 | Barbut et al. |
| 6,129,739 A | 10/2000 | Khosravi |
| 6,136,015 A | 10/2000 | Kurz |
| 6,136,016 A | 10/2000 | Barbut et al. |
| 6,142,987 A | 11/2000 | Tsugita |
| 6,152,946 A | 11/2000 | Broome et al. |
| 6,152,947 A | 11/2000 | Ambrisco et al. |
| 6,165,198 A | 12/2000 | McGurk et al. |
| 6,165,200 A | 12/2000 | Tsugita et al. |
| 6,168,579 B1 | 1/2001 | Tsugita et al. |
| 6,168,604 B1 | 1/2001 | Cano |
| 6,171,327 B1 | 1/2001 | Daniel et al. |
| 6,171,328 B1 | 1/2001 | Addis |
| 6,174,318 B1 | 1/2001 | Bates et al. |
| 6,176,849 B1 | 1/2001 | Yang et al. |
| 6,179,859 B1 | 1/2001 | Bates et al. |
| 6,179,860 B1 | 1/2001 | Fulton, III et al. |
| 6,179,861 B1 | 1/2001 | Khosravi et al. |
| 6,187,025 B1 | 2/2001 | Machek |
| 6,203,561 B1 | 3/2001 | Ramee et al. |
| 6,206,868 B1 | 3/2001 | Parodi |
| 6,214,026 B1 | 4/2001 | Lepak et al. |
| 6,224,620 B1 | 5/2001 | Maahs |
| 6,235,044 B1 | 5/2001 | Root et al. |
| 6,235,045 B1 | 5/2001 | Barbut et al. |
| 6,238,412 B1 | 5/2001 | Dubrul et al. |
| 6,241,746 B1 | 6/2001 | Bosma et al. |
| 6,245,012 B1 | 6/2001 | Kleshinski |
| 6,245,087 B1 | 6/2001 | Addis |
| 6,245,088 B1 | 6/2001 | Lowery |
| 6,245,089 B1 | 6/2001 | Daniel et al. |
| 6,251,122 B1 | 6/2001 | Tsukernik |
| 6,254,633 B1 | 7/2001 | Pinchuk et al. |
| 6,258,115 B1 | 7/2001 | Dubrul |
| 6,258,120 B1 | 7/2001 | McKenzie et al. |
| 6,264,663 B1 | 7/2001 | Cano |

| | | |
|---|---|---|
| 6,264,672 B1 | 7/2001 | Fisher |
| 6,267,776 B1 | 7/2001 | O'Connell |
| 6,267,777 B1 | 7/2001 | Bosma et al. |
| 6,270,477 B1 | 8/2001 | Bagaosian |
| 6,270,513 B1 | 8/2001 | Tsugita et al. |
| 6,273,901 B1 | 8/2001 | Whitcher et al. |
| 6,277,138 B1 | 8/2001 | Levinson et al. |
| 6,277,139 B1 | 8/2001 | Levinson et al. |
| 6,280,451 B1 | 8/2001 | Bates et al. |
| 6,209,710 B1 | 9/2001 | Cryer et al. |
| 6,287,321 B1 | 9/2001 | Jang |
| 6,290,656 B1 | 9/2001 | Boyle et al. |
| 6,295,989 B1 | 10/2001 | Connors, III |
| 6,306,163 B1 | 10/2001 | Fitz |
| 6,319,242 B1 | 11/2001 | Patterson et al. |
| 6,319,268 B1 | 11/2001 | Ambrisco et al. |
| 6,325,815 B1 | 12/2001 | Kusleika et al. |
| 6,336,934 B1 * | 1/2002 | Gilson et al. ............... 606/200 |
| 6,340,364 B2 | 1/2002 | Kanesaka |
| 6,340,465 B1 | 1/2002 | Hsu et al. |
| 6,346,116 B1 | 2/2002 | Brooks et al. |
| 6,348,056 B1 | 2/2002 | Bates et al. |
| 6,355,051 B1 | 3/2002 | Sisskind et al. |
| 6,361,545 B1 | 3/2002 | Macoviak et al. |
| 6,361,546 B1 | 3/2002 | Khosravi |
| 6,364,895 B1 | 4/2002 | Greenhalgh |
| 6,364,896 B1 | 4/2002 | Addis |
| 6,371,969 B1 | 4/2002 | Tsguita et al. |
| 6,371,970 B1 | 4/2002 | Khosravi et al. |
| 6,371,971 B1 | 4/2002 | Tsugita et al. |
| 6,375,670 B1 | 4/2002 | Greenhalgh |
| 6,383,206 B1 | 5/2002 | Gillick et al. |
| 6,384,062 B1 | 5/2002 | Ikeda et al. |
| 6,391,044 B1 | 5/2002 | Yadav et al. |
| 6,394,978 B1 | 5/2002 | Boyle et al. |
| 6,395,014 B1 | 5/2002 | Macoviak et al. |
| 6,398,756 B2 | 6/2002 | Peterson et al. |
| 6,402,771 B1 | 6/2002 | Palmer et al. |
| 6,406,471 B1 | 6/2002 | Jang et al. |
| 6,423,032 B2 | 7/2002 | Parodi |
| 6,423,086 B1 | 7/2002 | Barbut et al. |
| 6,425,909 B1 | 7/2002 | Dieck et al. |
| 6,428,559 B1 | 8/2002 | Johnson |
| 6,432,122 B1 | 8/2002 | Gilson et al. |
| 6,436,121 B1 | 8/2002 | Blom |
| 6,443,926 B1 | 9/2002 | Kletschka |
| 6,443,971 B1 | 9/2002 | Boylan et al. |
| 6,443,972 B1 | 9/2002 | Bosma |
| 6,443,979 B1 | 9/2002 | Stalker et al. |
| 6,447,530 B1 | 9/2002 | Ostrovsky et al. |
| 6,447,531 B1 | 9/2002 | Amplatz |
| 6,450,989 B2 | 9/2002 | Dubrul et al. |
| 6,458,139 B1 | 10/2002 | Palmer et al. |
| 6,461,370 B1 | 10/2002 | Gray et al. |
| 6,468,291 B2 | 10/2002 | Bates et al. |
| 6,482,222 B1 | 11/2002 | Bruckheimer et al. |
| 6,485,456 B1 | 11/2002 | Kletschka |
| 6,485,497 B2 | 11/2002 | Wensel et al. |
| 6,485,500 B1 | 11/2002 | Kokish et al. |
| 6,485,501 B1 | 11/2002 | Green |
| 6,485,502 B2 | 11/2002 | Don Michael et al. |
| 6,485,507 B1 | 11/2002 | Walak et al. |
| 6,635,070 B2 | 11/2002 | Evans et al. |
| 6,494,895 B2 | 12/2002 | Addis |
| 6,499,487 B1 | 12/2002 | McKenzie et al. |
| 6,500,166 B1 | 12/2002 | Zadno Azizi et al. |
| 6,506,203 B1 | 1/2003 | Boyle et al. |
| 6,506,205 B2 | 1/2003 | Goldberg et al. |
| 6,511,492 B1 | 1/2003 | Rosenbluth |
| 6,511,496 B1 | 1/2003 | Huter et al. |
| 6,511,497 B1 | 1/2003 | Braun et al. |
| 6,511,503 B1 | 1/2003 | Burkett et al. |
| 6,514,273 B1 | 2/2003 | Voss et al. |
| 6,517,550 B1 | 2/2003 | Konya et al. |
| 6,517,559 B1 | 2/2003 | O'Connell |
| 6,520,978 B1 | 2/2003 | Blackledge et al. |
| 6,527,746 B1 | 3/2003 | Oslund et al. |
| 6,527,791 B2 | 3/2003 | Fisher |
| 6,530,939 B1 | 3/2003 | Hopkins et al. |
| 6,530,940 B2 | 3/2003 | Fisher |
| 6,533,800 B1 | 3/2003 | Barbut |
| 6,537,294 B1 | 3/2003 | Boyle et al. |
| 6,537,295 B2 | 3/2003 | Petersen |
| 6,537,296 B2 | 3/2003 | Levinson et al. |
| 6,537,297 B2 | 3/2003 | Tsugita et al. |
| 6,540,722 B1 | 4/2003 | Boyle et al. |
| 6,540,767 B1 | 4/2003 | Walak et al. |
| 6,540,786 B2 | 4/2003 | Chibrac et al. |
| 6,544,276 B1 | 4/2003 | Azizi |
| 6,544,279 B1 | 4/2003 | Hopkins et al. |
| 6,544,280 B1 | 4/2003 | Daniel et al. |
| 6,547,759 B1 | 4/2003 | Fisher |
| 6,551,268 B1 | 4/2003 | Kaganov et al. |
| 6,551,341 B2 | 4/2003 | Boylan et al. |
| 6,551,342 B1 | 4/2003 | Shen et al. |
| 6,558,401 B1 | 5/2003 | Azizi |
| 6,558,405 B1 | 5/2003 | McInnes |
| 6,562,058 B2 | 5/2003 | Seguin |
| 6,565,591 B2 | 5/2003 | Kelly et al. |
| 6,569,184 B2 | 5/2003 | Huter |
| 6,575,995 B1 | 6/2003 | Huter et al. |
| 6,575,996 B1 | 6/2003 | Denison et al. |
| 6,575,997 B1 | 6/2003 | Palmer et al. |
| 6,582,447 B1 | 6/2003 | Patel et al. |
| 6,582,448 B1 | 6/2003 | Boyle et al. |
| 6,585,756 B1 | 7/2003 | Strecker |
| 6,589,263 B1 | 7/2003 | Hopkins et al. |
| 6,589,265 B1 | 7/2003 | Palmer et al. |
| 6,592,546 B1 | 7/2003 | Barbut et al. |
| 6,592,606 B2 | 7/2003 | Huter et al. |
| 6,592,607 B1 | 7/2003 | Palmer et al. |
| 6,592,616 B1 | 7/2003 | Stack et al. |
| 6,596,011 B2 | 7/2003 | Johnson et al. |
| 6,599,307 B1 * | 7/2003 | Huter et al. ............... 606/200 |
| 6,599,308 B2 | 7/2003 | Amplatz |
| 6,602,269 B2 | 8/2003 | Wallace et al. |
| 6,602,271 B2 | 8/2003 | Adams et al. |
| 6,602,272 B2 | 8/2003 | Boylan et al. |
| 6,602,273 B2 | 8/2003 | Marshall |
| 6,605,102 B1 | 8/2003 | Mazzocchi et al. |
| 6,605,111 B2 | 8/2003 | Bose et al. |
| 6,607,506 B2 | 8/2003 | Kletschka |
| 6,610,077 B1 | 8/2003 | Hancock et al. |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,682 B2 | 9/2003 | Joergensen et al. |
| 6,620,148 B1 | 9/2003 | Tsugita et al. |
| 6,620,182 B1 | 9/2003 | Khosravi |
| 6,623,450 B1 | 9/2003 | Dutta |
| 6,629,953 B1 | 10/2003 | Boyd |
| 6,632,236 B2 | 10/2003 | Hogendijk |
| 6,632,241 B1 | 10/2003 | Hancock et al. |
| 6,635,068 B1 | 10/2003 | Dubrul et al. |
| 6,638,293 B1 | 10/2003 | Makowner et al. |
| 6,638,294 B1 | 10/2003 | Palmer |
| 6,645,220 B1 | 11/2003 | Huter et al. |
| 6,645,221 B1 | 11/2003 | Richter |
| 6,645,223 B2 | 11/2003 | Boyle et al. |
| 6,645,224 B2 | 11/2003 | Gilson et al. |
| 6,652,480 B1 | 11/2003 | Imran et al. |
| 6,652,505 B1 | 11/2003 | Tsugita et al. |
| 6,652,554 B1 | 11/2003 | Wholey et al. |
| 6,652,557 B1 | 11/2003 | MacDonald |
| 6,656,202 B2 * | 12/2003 | Papp et al. ............... 606/200 |
| 6,656,203 B2 | 12/2003 | Roth et al. |

| Patent No. | Date | Inventor(s) |
|---|---|---|
| 6,656,204 B2 | 12/2003 | Ambrisco et al. |
| 6,656,351 B2 | 12/2003 | Boyle |
| 6,660,021 B1 | 12/2003 | Palmer et al. |
| 6,663,650 B2 | 12/2003 | Sepetka et al. |
| 6,663,651 B2 | 12/2003 | Krolik et al. |
| 6,663,652 B2 | 12/2003 | Daniel et al. |
| 6,672,090 B1 | 1/2004 | Healy et al. |
| 6,676,666 B2 | 1/2004 | Vrba et al. |
| 6,676,682 B1 | 1/2004 | Tsugita et al. |
| 6,676,683 B1 | 1/2004 | Addis |
| 6,679,902 B1 | 1/2004 | Boyle et al. |
| 6,679,903 B2 | 1/2004 | Kurz |
| 6,682,546 B2 | 1/2004 | Amplatz |
| 6,685,722 B1 | 2/2004 | Rosenbluth et al. |
| 6,689,151 B2 | 2/2004 | Becker et al. |
| 6,692,513 B2 | 2/2004 | Streeter et al. |
| 6,695,813 B1 | 2/2004 | Boyle et al. |
| 6,695,858 B1 | 2/2004 | Dubrul et al. |
| 6,695,864 B2 | 2/2004 | Macoviak et al. |
| 6,696,666 B2 | 2/2004 | Merdan et al. |
| 6,699,260 B2 | 3/2004 | Dubrul et al. |
| 6,702,834 B1 * | 3/2004 | Boylan et al. ............... 606/200 |
| 6,706,055 B2 | 3/2004 | Douk et al. |
| 6,712,834 B2 | 3/2004 | Yassour et al. |
| 6,712,835 B2 | 3/2004 | Mazzocchi et al. |
| 6,716,231 B1 | 4/2004 | Rafiee et al. |
| 6,723,085 B2 | 4/2004 | Jang et al. |
| 6,726,701 B2 | 4/2004 | Gilson et al. |
| 6,726,702 B2 | 4/2004 | Khosravi |
| 6,726,703 B2 | 4/2004 | Broome et al. |
| 6,740,061 B1 | 5/2004 | Oslund et al. |
| 6,743,247 B1 | 6/2004 | Levinson et al. |
| 6,746,469 B2 | 6/2004 | Mouw |
| 6,752,819 B1 | 6/2004 | Brady et al. |
| 6,755,846 B1 | 6/2004 | Yadav |
| 6,758,855 B2 | 7/2004 | Fulton, III et al. |
| 6,761,727 B1 | 7/2004 | Ladd |
| 6,773,448 B2 | 8/2004 | Kusleika et al. |
| 6,790,219 B1 | 9/2004 | Murphy |
| 6,793,666 B2 | 9/2004 | Hansen et al. |
| 6,793,668 B1 | 9/2004 | Fisher |
| 6,800,080 B1 | 10/2004 | Bates |
| 6,814,739 B2 | 11/2004 | Secrest et al. |
| 6,818,006 B2 | 11/2004 | Douk et al. |
| 6,837,898 B2 | 1/2005 | Boyle |
| 6,840,950 B2 | 1/2005 | Stanford et al. |
| 6,843,798 B2 | 1/2005 | Kusleika et al. |
| 6,846,316 B2 | 1/2005 | Abrams |
| 6,846,317 B1 | 1/2005 | Nigon |
| 6,863,696 B2 | 3/2005 | Kantsevitcha |
| 6,866,677 B2 | 3/2005 | Douk et al. |
| 6,872,216 B2 | 3/2005 | Daniel et al. |
| 6,878,151 B2 | 4/2005 | Carrison et al. |
| 6,878,153 B2 | 4/2005 | Linder et al. |
| 6,887,256 B2 | 5/2005 | Gilson et al. |
| 6,887,257 B2 | 5/2005 | Salaheih et al. |
| 6,887,258 B2 | 5/2005 | Denison |
| 6,888,098 B1 | 5/2005 | Merdan et al. |
| 6,890,340 B2 | 5/2005 | Duane |
| 6,890,341 B2 | 5/2005 | Dieck et al. |
| 6,893,450 B2 | 5/2005 | Foster |
| 6,893,451 B2 | 5/2005 | Cano et al. |
| 6,896,690 B1 | 5/2005 | Lambrecht et al. |
| 6,896,691 B2 | 5/2005 | Boylan |
| 6,902,540 B2 | 6/2005 | Dorros et al. |
| 6,908,474 B2 | 6/2005 | Hogendijk et al. |
| 6,911,036 B2 | 6/2005 | Douk et al. |
| 6,913,612 B2 | 7/2005 | Palmer et al. |
| 6,918,921 B2 | 7/2005 | Brady et al. |
| 6,929,652 B1 | 8/2005 | Andrews |
| 6,932,830 B2 | 8/2005 | Ungs |
| 6,932,831 B2 | 8/2005 | Forber |
| 6,936,058 B2 | 8/2005 | Forde et al. |
| 6,936,059 B2 | 8/2005 | Belef |
| 6,939,361 B1 | 9/2005 | Kleshinski |
| 6,939,362 B2 | 9/2005 | Boyle et al. |
| 6,942,673 B2 | 9/2005 | Bates et al. |
| 6,949,103 B2 | 9/2005 | Mazzocchi et al. |
| 6,951,570 B2 | 10/2005 | Linder et al. |
| 6,953,471 B1 | 10/2005 | Lilly et al. |
| 6,953,472 B2 | 10/2005 | Palmer et al. |
| 6,958,074 B2 | 10/2005 | Russell |
| 6,960,370 B2 | 11/2005 | Monni et al. |
| 6,962,598 B2 | 11/2005 | Linder et al. |
| 6,964,670 B1 | 11/2005 | Shah |
| 6,964,672 B2 | 11/2005 | Brady |
| 6,964,673 B2 | 11/2005 | Tsugita et al. |
| 6,969,395 B2 | 11/2005 | Eskuri |
| 6,969,396 B2 | 11/2005 | Krolik et al. |
| 6,969,402 B2 | 11/2005 | Bales et al. |
| 6,970,730 B2 | 11/2005 | Fuimaono et al. |
| 6,972,025 B2 | 12/2005 | WasDyke |
| 6,973,340 B2 | 12/2005 | Fuimaono et al. |
| 6,974,468 B2 | 12/2005 | DoBrava et al. |
| 6,974,469 B2 | 12/2005 | Broome et al. |
| 6,979,343 B2 | 12/2005 | Russo |
| 6,979,344 B2 | 12/2005 | Jones et al. |
| 6,986,778 B2 | 1/2006 | Zadno-Azizi |
| 6,989,021 B2 | 1/2006 | Bosma et al. |
| 6,989,027 B2 | 1/2006 | Allen et al. |
| 6,991,641 B2 | 1/2006 | Diaz et al. |
| 6,991,642 B2 | 1/2006 | Petersen |
| 9,989,019 | 1/2006 | Mazzocchi |
| RE38,972 E | 2/2006 | Purdy |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,001,407 B2 | 2/2006 | Hansen et al. |
| 7,004,954 B2 | 2/2006 | Voss et al. |
| 7,004,955 B2 | 2/2006 | Shen et al. |
| 7,004,956 B2 | 2/2006 | Palmer et al. |
| 7,004,964 B2 | 2/2006 | Thompson et al. |
| 7,011,671 B2 | 3/2006 | Welch |
| 7,011,672 B2 | 3/2006 | Barbut et al. |
| 7,014,647 B2 | 3/2006 | Brady et al. |
| 7,018,372 B2 | 3/2006 | Casey et al. |
| 7,018,385 B2 | 3/2006 | Bates et al. |
| 7,018,393 B1 | 3/2006 | Boyle et al. |
| 7,029,440 B2 | 4/2006 | Broome et al. |
| 7,033,375 B2 | 4/2006 | Mazzocchi et al. |
| 7,037,320 B2 | 5/2006 | Brady et al. |
| 7,041,116 B2 | 5/2006 | Goto et al. |
| 7,044,958 B2 | 5/2006 | Douk et al. |
| 7,048,752 B2 | 5/2006 | Mazzocchi |
| 7,048,758 B2 | 5/2006 | Boyle et al. |
| 7,056,328 B2 | 6/2006 | Arnott |
| 7,060,082 B2 | 6/2006 | Goll et al. |
| 7,077,854 B2 | 7/2006 | Khosravi |
| 7,094,243 B2 | 8/2006 | Mulholland |
| 7,094,249 B2 | 8/2006 | Broome et al. |
| 7,097,440 B2 | 8/2006 | Boyle et al. |
| 7,097,651 B2 | 8/2006 | Harrison et al. |
| 7,101,379 B2 | 9/2006 | Gregory, Jr et al. |
| 7,101,380 B2 | 9/2006 | Khachin et al. |
| 7,108,707 B2 | 9/2006 | Huter et al. |
| 2002/0091408 A1 | 7/2002 | Sutton et al. |
| 2002/0091409 A1 | 7/2002 | Sutton et al. |
| 2002/0095141 A1 | 7/2002 | Belef et al. |
| 2002/0099407 A1 | 7/2002 | Becker et al. |
| 2002/0103501 A1 | 8/2002 | Diaz et al. |
| 2002/0107541 A1 | 8/2002 | Vale et al. |
| 2002/0111648 A1 | 8/2002 | Kusleika et al. |
| 2002/0111659 A1 | 8/2002 | Russo et al. |
| 2002/0115942 A1 | 8/2002 | Stanford et al. |
| 2002/0120286 A1 | 8/2002 | Dobrava et al. |

| | | | | | |
|---|---|---|---|---|---|
| 2002/0121472 A1 | 9/2002 | Garner et al. | 2003/0135162 A1 | 7/2003 | Deyette, Jr. et al. |
| 2002/0123720 A1 | 9/2002 | Kusleika et al. | 2003/0135232 A1 | 7/2003 | Douk et al. |
| 2002/0123755 A1 | 9/2002 | Lowe et al. | 2003/0139764 A1 | 7/2003 | Levinson et al. |
| 2002/0128679 A1 | 9/2002 | Turovskiy et al. | 2003/0144685 A1 | 7/2003 | Boyle et al. |
| 2002/0128680 A1 | 9/2002 | Pavlovic | 2003/0150821 A1 | 8/2003 | Bates et al. |
| 2002/0128681 A1 | 9/2002 | Broome et al. | 2003/0153935 A1 | 8/2003 | Mialhe |
| 2002/0133092 A1 | 9/2002 | Oslund et al. | 2003/0153942 A1 | 8/2003 | Wang et al. |
| 2002/0138094 A1 | 9/2002 | Borillo et al. | 2003/0153943 A1 | 8/2003 | Michael et al. |
| 2002/0138095 A1 | 9/2002 | Mazzocchi et al. | 2003/0158574 A1 | 8/2003 | Esch et al. |
| 2002/0143360 A1 | 10/2002 | Douk et al. | 2003/0163064 A1 | 8/2003 | Vrba et al. |
| 2002/0143361 A1 | 10/2002 | Douk et al. | 2003/0171770 A1 | 9/2003 | Anderson et al. |
| 2002/0151927 A1 | 10/2002 | Douk et al. | 2003/0171771 A1 | 9/2003 | Shimon |
| 2002/0156456 A1 | 10/2002 | Fisher | 2003/0171803 A1 | 9/2003 | Berrada et al. |
| 2002/0156457 A1 | 10/2002 | Fisher | 2003/0176884 A1 | 9/2003 | Broome et al. |
| 2002/0161390 A1 | 10/2002 | Mouw | 2003/0176885 A1 | 9/2003 | Wholey et al. |
| 2002/0161392 A1 | 10/2002 | Dubrul | 2003/0176886 A1 | 9/2003 | Sutton et al. |
| 2002/0161393 A1 | 10/2002 | Demond et al. | 2003/0176889 A1 | 9/2003 | Boyle et al. |
| 2002/0161395 A1 | 10/2002 | Douk et al. | 2003/0181942 A1 | 9/2003 | Daniel et al. |
| 2002/0165576 A1 | 11/2002 | Boyle et al. | 2003/0181943 A1 | 9/2003 | Daniel et al. |
| 2002/0169414 A1 | 11/2002 | Kletschka | 2003/0187474 A1 | 10/2003 | Keegan et al. |
| 2002/0169458 A1 | 11/2002 | Connors, III | 2003/0187475 A1 | 10/2003 | Tsugita et al. |
| 2002/0169472 A1 | 11/2002 | Douk et al. | 2003/0187495 A1 | 10/2003 | Cully et al. |
| 2002/0169474 A1 | 11/2002 | Kusleika et al. | 2003/0191493 A1 | 10/2003 | Epstein et al. |
| 2002/0173815 A1 | 11/2002 | Hogendijk et al. | 2003/0195554 A1 | 10/2003 | Shen et al. |
| 2002/0173817 A1 | 11/2002 | Kletschka et al. | 2003/0195555 A1 | 10/2003 | Khairkhahan et al. |
| 2002/0188313 A1 | 12/2002 | Johnson et al. | 2003/0195556 A1 | 10/2003 | Stack et al. |
| 2002/0188314 A1 | 12/2002 | Anderson et al. | 2003/0199819 A1 | 10/2003 | Beck |
| 2002/0193825 A1 | 12/2002 | McGuckin et al. | 2003/0199921 A1 | 10/2003 | Palmer et al. |
| 2002/0193826 A1 | 12/2002 | McGuckin et al. | 2003/0204168 A1 | 10/2003 | Bosme et al. |
| 2002/0193827 A1 | 12/2002 | McGuckin et al. | 2003/0204202 A1 | 10/2003 | Palmer et al. |
| 2002/0193828 A1 | 12/2002 | Griffin et al. | 2003/0208222 A1 | 11/2003 | Zadno-Azizi |
| 2003/0004536 A1 | 1/2003 | Boylan et al. | 2003/0208224 A1 | 11/2003 | Broome |
| 2003/0004537 A1 | 1/2003 | Boyle et al. | 2003/0208225 A1 | 11/2003 | Goll et al. |
| 2003/0004539 A1 | 1/2003 | Linder et al. | 2003/0208226 A1 | 11/2003 | Bruckheimer et al. |
| 2003/0004540 A1 | 1/2003 | Linder et al. | 2003/0208227 A1 | 11/2003 | Thomas |
| 2003/0004541 A1 | 1/2003 | Linder et al. | 2003/0208228 A1 | 11/2003 | Gilson et al. |
| 2003/0009188 A1 | 1/2003 | Linder et al. | 2003/0208229 A1 | 11/2003 | Kletschka |
| 2003/0009189 A1 | 1/2003 | Gilson et al. | 2003/0212361 A1 | 11/2003 | Boyle et al. |
| 2003/0015203 A1 | 1/2003 | Roth et al. | 2003/0212429 A1 | 11/2003 | Keegan et al. |
| 2003/0018354 A1 | 1/2003 | Roth et al. | 2003/0212431 A1 | 11/2003 | Brady et al. |
| 2003/0023265 A1 | 1/2003 | Forber | 2003/0212434 A1 | 11/2003 | Thielen |
| 2003/0028238 A1 | 2/2003 | Burkett et al. | 2003/0216774 A1 | 11/2003 | Larson |
| 2003/0032941 A1 | 2/2003 | Boyle et al. | 2003/0220665 A1 | 11/2003 | Eskuri et al. |
| 2003/0032977 A1 | 2/2003 | Brady et al. | 2003/0225418 A1 | 12/2003 | Eskuri et al. |
| 2003/0040772 A1 | 2/2003 | Hyodoh et al. | 2003/0225435 A1 | 12/2003 | Huter et al. |
| 2003/0042186 A1 | 3/2003 | Boyle et al. | 2003/0229295 A1 | 12/2003 | Houde et al. |
| 2003/0045898 A1 | 3/2003 | Harrison et al. | 2003/0229374 A1 | 12/2003 | Brady et al. |
| 2003/0057156 A1 | 3/2003 | Peterson et al. | 2003/0233117 A1 | 12/2003 | Adams et al. |
| 2003/0060782 A1 | 3/2003 | Bose et al. | 2003/0236545 A1 | 12/2003 | Gilson |
| 2003/0060843 A1 | 3/2003 | Boucher | 2004/0002730 A1 | 1/2004 | Denison et al. |
| 2003/0060844 A1 | 3/2003 | Borillo et al. | 2004/0006361 A1 | 1/2004 | Boyle et al. |
| 2003/0065354 A1 | 4/2003 | Boyle et al. | 2004/0006364 A1 | 1/2004 | Ladd |
| 2003/0069596 A1 | 4/2003 | Eskuri | 2004/0006365 A1 | 1/2004 | Brady et al. |
| 2003/0069597 A1 | 4/2003 | Petersen | 2004/0006366 A1 | 1/2004 | Huter et al. |
| 2003/0078519 A1 | 4/2003 | Salahieh et al. | 2004/0006367 A1 | 1/2004 | Johnson et al. |
| 2003/0078614 A1 | 4/2003 | Satahieh et al. | 2004/0006368 A1 | 1/2004 | Mazzocchi et al. |
| 2003/0083692 A1 | 5/2003 | Vrba et al. | 2004/0015184 A1 | 1/2004 | Boyle et al. |
| 2003/0083693 A1 | 5/2003 | Daniel et al. | 2004/0019363 A1 | 1/2004 | Hanson et al. |
| 2003/0100917 A1 | 5/2003 | Boyle et al. | 2004/0034385 A1 | 2/2004 | Gilson et al. |
| 2003/0100918 A1 | 5/2003 | Duane | 2004/0039411 A1 | 2/2004 | Gilson et al. |
| 2003/0105484 A1 | 6/2003 | Boyle et al. | 2004/0044359 A1 | 3/2004 | Renati et al. |
| 2003/0109824 A1 | 6/2003 | Anderson et al. | 2004/0044360 A1 | 3/2004 | Lowe |
| 2003/0114879 A1 | 6/2003 | Euteneuer et al. | 2004/0049226 A1 | 3/2004 | Keegan et al. |
| 2003/0114880 A1 | 6/2003 | Hansen et al. | 2004/0059372 A1 | 3/2004 | Tsugita |
| 2003/0120303 A1 | 6/2003 | Boyle et al. | 2004/0059373 A1 | 3/2004 | Shapiro et al. |
| 2003/0130680 A1 | 7/2003 | Russell | 2004/0082697 A1 | 4/2004 | Broome et al. |
| 2003/0130681 A1 | 7/2003 | Ungs | 2004/0082968 A1 | 4/2004 | Krolik et al. |
| 2003/0130682 A1 | 7/2003 | Broome et al. | 2004/0088000 A1 | 5/2004 | Muller |
| 2003/0130684 A1 | 7/2003 | Brady et al. | 2004/0088002 A1 | 5/2004 | Boyle et al. |
| 2003/0130685 A1 | 7/2003 | Daniel et al. | 2004/0093009 A1 | 5/2004 | Denison et al. |
| 2003/0130686 A1 | 7/2003 | Daniel et al. | 2004/0093010 A1 | 5/2004 | Gesswein et al. |
| 2003/0130687 A1 | 7/2003 | Daniel et al. | 2004/0093011 A1 | 5/2004 | Vrba |
| 2003/0130688 A1 | 7/2003 | Daniel et al. | 2004/0093012 A1 | 5/2004 | Cully et al. |

| | | | | | | |
|---|---|---|---|---|---|---|
| 2004/0093013 A1 | 5/2004 | Brady et al. | | 2005/0101989 A1 | 5/2005 | Cully et al. |
| 2004/0098022 A1 | 5/2004 | Barone | | 2005/0113865 A1 | 5/2005 | Daniel et al. |
| 2004/0098026 A1 | 5/2004 | Joergensen et al. | | 2005/0119688 A1 | 6/2005 | Bergheim |
| 2004/0098032 A1 | 5/2004 | Papp et al. | | 2005/0119689 A1 | 6/2005 | Mazzocchi et al. |
| 2004/0098033 A1 | 5/2004 | Leeflang et al. | | 2005/0119690 A1 | 6/2005 | Mazzocchi et al. |
| 2004/0102807 A1 | 5/2004 | Kusleika et al. | | 2005/0119691 A1 | 6/2005 | Daniel et al. |
| 2004/0106944 A1 | 6/2004 | Daniel et al. | | 2005/0124931 A1 | 6/2005 | Fulton et al. |
| 2004/0111111 A1 | 6/2004 | Lin | | 2005/0125023 A1 | 6/2005 | Bates et al. |
| 2004/0116960 A1 | 6/2004 | Demond et al. | | 2005/0131450 A1 | 6/2005 | Nicholson et al. |
| 2004/0122466 A1 | 6/2004 | Bales | | 2005/0131453 A1 | 6/2005 | Parodi |
| 2004/0127933 A1 | 7/2004 | Demond et al. | | 2005/0149110 A1 | 7/2005 | Wholey et al. |
| 2004/0127934 A1 | 7/2004 | Gilson et al. | | 2005/0149112 A1 | 7/2005 | Barbut |
| 2004/0127936 A1 | 7/2004 | Salaheih et al. | | 2005/0149113 A1 | 7/2005 | Douk et al. |
| 2004/0138693 A1 | 7/2004 | Eskuri et al. | | 2005/0159772 A1 | 7/2005 | Lowe et al. |
| 2004/0138694 A1 | 7/2004 | Tran et al. | | 2005/0159773 A1 | 7/2005 | Broome et al. |
| 2004/0138696 A1 | 7/2004 | Drasler et al. | | 2005/0159774 A1 | 7/2005 | Belef |
| 2004/0144689 A1 | 7/2004 | Brady et al. | | 2005/0171573 A1 | 8/2005 | Salahich et al. |
| 2004/0147955 A1 | 7/2004 | Beulke et al. | | 2005/0177187 A1 | 8/2005 | Gray et al. |
| 2004/0153118 A1 | 8/2004 | Clubb et al. | | 2005/0182440 A1 | 8/2005 | Bates et al. |
| 2004/0153119 A1 | 8/2004 | Kusleika et al. | | 2005/0182441 A1 | 8/2005 | Denison et al. |
| 2004/0158275 A1 | 8/2004 | Crank et al. | | 2005/0192623 A1 | 9/2005 | Mazzocchi et al. |
| 2004/0158277 A1 | 8/2004 | Lowe et al. | | 2005/0192624 A1 | 9/2005 | Mazzocchi et al. |
| 2004/0158278 A1 | 8/2004 | Becker et al. | | 2005/0203567 A1 | 9/2005 | Linder |
| 2004/0158279 A1 | 8/2004 | Petersen | | 2005/0203568 A1 | 9/2005 | Burg et al. |
| 2004/0158280 A1 | 8/2004 | Morris et al. | | 2005/0203569 A1 | 9/2005 | Kusleika et al. |
| 2004/0158281 A1 | 8/2004 | Boylan et al. | | 2005/0203570 A1 | 9/2005 | Mazzocchi et al. |
| 2004/0167564 A1 | 8/2004 | Fedie | | 2005/0203571 A1 | 9/2005 | Mazzocchi et al. |
| 2004/0167565 A1 | 8/2004 | Beulke et al. | | 2005/0209634 A1 | 9/2005 | Brady et al. |
| 2004/0167566 A1 | 8/2004 | Beulke et al. | | 2005/0209635 A1 | 9/2005 | Gilson et al. |
| 2004/0167567 A1 | 8/2004 | Cano et al. | | 2005/0216051 A1 | 9/2005 | Mazzocchi et al. |
| 2004/0167568 A1 | 8/2004 | Boylan et al. | | 2005/0216052 A1 | 9/2005 | Mazzocchi et al. |
| 2004/0172055 A1 | 9/2004 | Huter et al. | | 2005/0216053 A1 | 9/2005 | Douk et al. |
| 2004/0176794 A1 | 9/2004 | Khosravi | | 2005/0222583 A1 | 10/2005 | Cano et al. |
| 2004/0193208 A1 | 9/2004 | Talpade et al. | | 2005/0222604 A1 | 10/2005 | Schaeffer et al. |
| 2004/0199198 A1 | 10/2004 | Beulke et al. | | 2005/0222607 A1 | 10/2005 | Palmer et al. |
| 2004/0199199 A1 | 10/2004 | Krolik et al. | | 2005/0228437 A1 | 10/2005 | Gilson et al. |
| 2004/0199203 A1 | 10/2004 | Oslund et al. | | 2005/0228438 A1 | 10/2005 | Sachar et al. |
| 2004/0204737 A1 | 10/2004 | Boismier et al. | | 2005/0228439 A1 | 10/2005 | Andrews et al. |
| 2004/0210250 A1 | 10/2004 | Eskuri | | 2005/0234502 A1 | 10/2005 | Gilson et al. |
| 2004/0220608 A1 | 11/2004 | D'Aquanni et al. | | 2005/0240215 A1 | 10/2005 | Ellis |
| 2004/0220609 A1 | 11/2004 | Douk et al. | | 2005/0245866 A1 | 11/2005 | Azizi |
| 2004/0220611 A1 | 11/2004 | Ogle | | 2005/0267517 A1 | 12/2005 | Ungs |
| 2004/0225322 A1 | 11/2004 | Garrison et al. | | 2005/0283184 A1 | 12/2005 | Gilson et al. |
| 2004/0236368 A1 | 11/2004 | McGucklin, Jr. et al. | | 2005/0283185 A1 | 12/2005 | Linder et al. |
| 2004/0236369 A1 | 11/2004 | Dubrul | | 2005/0283186 A1 | 12/2005 | Berrada et al. |
| 2004/0249409 A1 | 12/2004 | Krolik et al. | | 2005/0288705 A1 | 12/2005 | Gilson et al. |
| 2004/0254601 A1 | 12/2004 | Eskuri | | 2006/0004403 A1 | 1/2006 | Gilson et al. |
| 2004/0254602 A1 | 12/2004 | Lehe et al. | | 2006/0004405 A1 | 1/2006 | Salaheih |
| 2004/0260308 A1 | 12/2004 | Gilson et al. | | 2006/0015138 A1 | 1/2006 | Getner et al. |
| 2004/0260333 A1 | 12/2004 | Dubrul et al. | | 2006/0015139 A1 | 1/2006 | Tsugita et al. |
| 2004/0267301 A1 | 12/2004 | Boylan et al. | | 2006/0015141 A1 | 1/2006 | Linder et al. |
| 2004/0267302 A1 | 12/2004 | Gilson et al. | | 2006/0020285 A1 | 1/2006 | Niermann |
| 2005/0004594 A1 | 1/2005 | Nool et al. | | 2006/0020286 A1 | 1/2006 | Niermann |
| 2005/0004595 A1 | 1/2005 | Boyle et al. | | 2006/0025803 A1 | 2/2006 | Mitelberg et al. |
| 2005/0004597 A1 | 1/2005 | McGuckin, Jr. et al. | | 2006/0025804 A1 | 2/2006 | Krolik et al. |
| 2005/0010245 A1 | 1/2005 | Wasicek | | 2006/0025805 A1 | 2/2006 | DoBrava et al. |
| 2005/0010246 A1 | 1/2005 | Steeter et al. | | 2006/0030876 A1 | 2/2006 | Peacock, III et al. |
| 2005/0010247 A1 | 1/2005 | Kusleika et al. | | 2006/0030877 A1 | 2/2006 | Martinez et al. |
| 2005/0021075 A1 | 1/2005 | Bonnette et al. | | 2006/0030878 A1 | 2/2006 | Anderson et al. |
| 2005/0021076 A1 | 1/2005 | Mazzocchi et al. | | 2006/0052817 A1 | 3/2006 | Russo et al. |
| 2005/0055048 A1 | 3/2005 | Dieck et al. | | 2006/0074446 A1 | 4/2006 | Gilson et al. |
| 2005/0070953 A1 | 3/2005 | Riley | | 2006/0095069 A1 | 5/2006 | Shah et al. |
| 2005/0075663 A1 | 4/2005 | Boyle et al. | | 2006/0100659 A1 | 5/2006 | Dinh et al. |
| 2005/0080446 A1 | 4/2005 | Gilson et al. | | 2006/0100662 A1 | 5/2006 | Daniel et al. |
| 2005/0085842 A1 | 4/2005 | Eversull et al. | | 2006/0100663 A1 | 5/2006 | Palmer et al. |
| 2005/0090845 A1 | 4/2005 | Boyd | | 2006/0116715 A1 | 6/2006 | Khosravi et al. |
| 2005/0090857 A1 | 4/2005 | Kusleika et al. | | 2006/0122643 A1 | 6/2006 | Wasicek |
| 2005/0090858 A1 | 4/2005 | Pavlovic | | 2006/0122644 A1 | 6/2006 | Brady et al. |
| 2005/0096691 A1 | 5/2005 | Groothuis et al. | | 2006/0122645 A1 | 6/2006 | Brady et al. |
| 2005/0096692 A1 | 5/2005 | Linder et al. | | 2006/0129181 A1 | 6/2006 | Callol et al. |
| 2005/0101986 A1 | 5/2005 | Daniel et al. | | 2006/0129182 A1 | 6/2006 | Gilson et al. |
| 2005/0101987 A1 | 5/2005 | Salahich | | 2006/0129183 A1 | 6/2006 | Boyle et al. |
| 2005/0101988 A1 | 5/2005 | Stanford et al. | | 2006/0149312 A1 | 7/2006 | Arguello et al. |

| | | | | | | |
|---|---|---|---|---|---|---|
| 2006/0149313 A1 | 7/2006 | Arguello et al. | EP | 0533511 A1 | 3/1993 | |
| 2006/0149314 A1 | 7/2006 | Borillo et al. | FR | 2580504 A1 | 10/1986 | |
| 2006/0155322 A1 | 7/2006 | Sater et al. | GB | 2020557 | 11/1979 | |
| 2006/0161198 A1 | 7/2006 | Sakai et al. | WO | WO92/03097 | 3/1992 | |
| 2006/0167491 A1 | 7/2006 | Wholey et al. | WO | WO96/01591 | 1/1996 | |
| 2006/0184194 A1 | 8/2006 | Pal et al. | WO | WO97/17100 | 5/1997 | |
| 2006/0190025 A1 | 8/2006 | Lehe et al. | WO | WO98/02084 | 1/1998 | |
| 2006/0195137 A1 | 8/2006 | Sepetka et al. | WO | WO98/33443 | 8/1998 | |
| 2006/0195138 A1 | 8/2006 | Goll et al. | WO | WO99/23976 | 5/1999 | |
| 2006/0200047 A1 | 9/2006 | Galdonik et al. | WO | WO99/44510 | 9/1999 | |
| 2006/0200191 A1 | 9/2006 | Zadno-Azizi | WO | WO00/67667 | 11/2000 | |
| 2006/0206139 A1 | 9/2006 | Tekulve | WO | WO01/10346 | 2/2001 | |

FOREIGN PATENT DOCUMENTS

| | | | |
|---|---|---|---|
| | | WO | WO01/45592 | 6/2001 |
| | | WO | WO01/87183 | 11/2001 |
| EP | 0472334 A1 | 2/1992 | * cited by examiner |

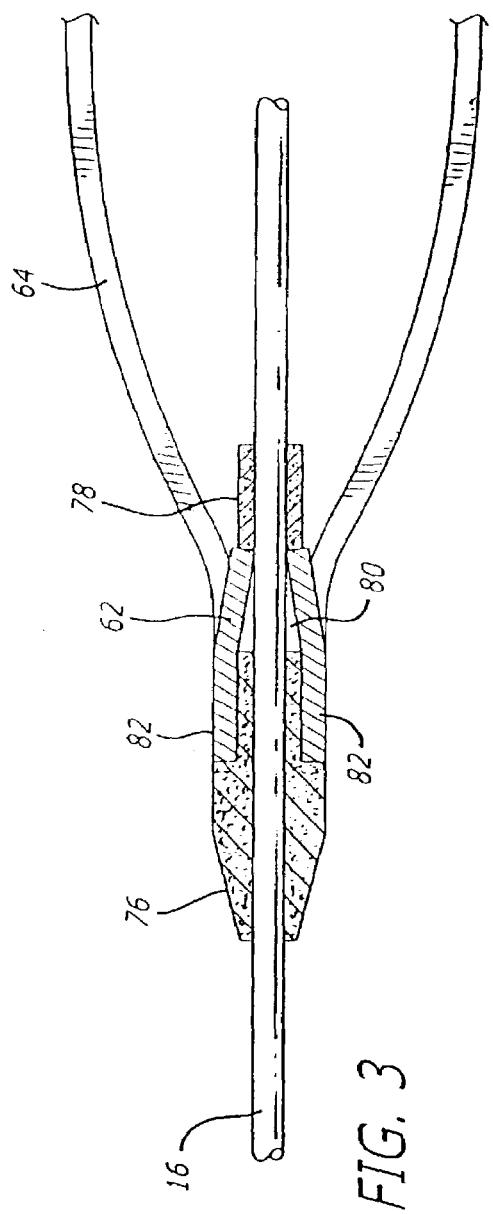
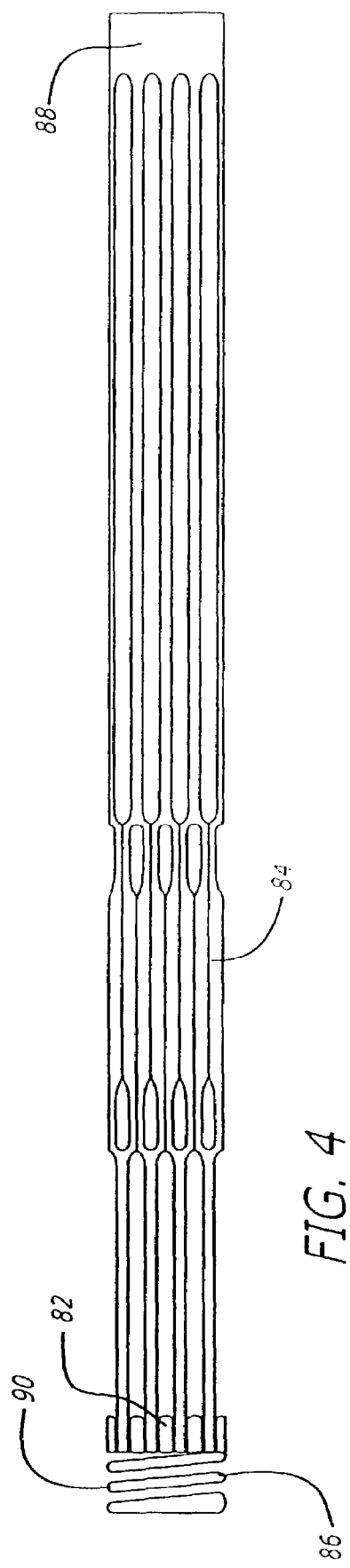

FILTER DEVICE FOR EMBOLIC PROTECTION SYSTEMS

This application is a continuation of application Ser. No. 09/919,503 filed Jul. 31, 2001 which is a continuation-in-part of application Ser. No. 09/896,142 filed on Jun. 29, 2001.

BACKGROUND OF THE INVENTION

The present invention relates generally to improvements in embolic protection systems and methods. In particular, it relates to an improved system and method for enabling an embolic protection device to be efficiently and conveniently engaged with the distal end of a guide wire. The system also enables the device to effectively expand against the inner surface of a blood vessel wall, and to seal off the inner surface thereof upon deployment thereof at a location distal to an interventional procedure site. Such deployment enables the efficient capture of embolic material, which may be created and released into the bloodstream during the performance of the interventional procedure in a stenosed or occluded region of a blood vessel, and prevents embolic material from bypassing the embolic protection device. The system further enables the embolic protection device to provide a reference for the effective positioning thereof at the location distal to the interventional procedure site. It also is formed of expandable material for enabling efficient expansion thereof, and includes a portion thereof formed so as to be in tension, such that another portion thereof is in compression, to effectively assist in enabling the system to bend in tortuous vasculature.

The systems and methods of the present invention are particularly useful when performing balloon angioplasty, stenting procedures, laser angioplasty or atherectomy in critical vessels, such as the carotid, renal, and saphenous vein graft arteries, where the release of embolic debris into the bloodstream could possibly occlude the flow of oxygenated blood to the brain or other vital organs which can cause devastating consequences to the patient.

A variety of non-surgical interventional procedures have been developed over the years for opening stenosed or occluded blood vessels in a patient caused by the build up of plaque or other substances on the walls of the blood vessel. Such procedures usually involve the percutaneous introduction of the interventional device into the lumen of the artery, usually through a catheter. One widely known and medically accepted procedure is balloon angioplasty in which an inflatable balloon is introduced within the stenosed region of the blood vessel to dilate the occluded vessel. The balloon catheter is initially inserted into the patient's arterial system and is advanced and manipulated into the area of stenosis in the artery. The balloon is inflated to compress the plaque and press the vessel wall radially outward to increase the diameter of the blood vessel.

Another procedure is laser angioplasty which utilizes a laser to ablate the stenosis by super heating and vaporizing the deposited plaque. Atherectomy is yet another method of treating a stenosed blood vessel in which a cutting blade is rotated to shave the deposited plaque from the arterial wall. A vacuum catheter may be used to capture the shaved plaque or thrombus from the blood stream during this procedure.

In another widely practiced procedure, the stenosis can be treated by placing a device known as a stent into the stenosed region to hold open and sometimes expand the segment of the blood vessel or other arterial lumen. Stents are particularly useful in the treatment or repair of blood vessels after a stenosis has been compressed by percutaneous transluminal coronary angioplasty (PTCA), percutaneous transluminal angioplasty (PTA) or removal by atherectomy or other means. Stents are usually delivered in a compressed condition to the target site, and then are deployed at the target location into an expanded condition to support the vessel and help maintain it in an open position.

In the past, stents typically have fallen into two general categories of construction. The first type of stent is expandable upon application of a controlled force, often through the inflation of the balloon portion of a dilatation catheter which, upon inflation of the balloon or other expansion means, expands the compressed stent to a larger diameter to be left in place within the artery at the target site. The second type of stent is a self-expanding stent formed from, for example, shape memory metals or super-elastic nickel-titanium (NiTi) alloys, which will automatically expand from a compressed state when the stent is advanced out of the distal end of the delivery catheter into the body lumen. Such stents manufactured from self-expandable materials allow for phase transformations of the material to occur, contributing to the expansion and contraction of the stent.

The above non-surgical interventional procedures, when successful, avoid the necessity of major surgical operations. However, there is one common problem associated with all of these non-surgical procedures, namely, the potential release of embolic debris into the bloodstream which can occlude distal vasculature and cause significant health problems to the patient. For example, during deployment of a stent, it is possible that the metal struts of the stent can cut into the stenosis and shear off pieces of plaque which become embolic debris that can travel downstream and lodge somewhere in the patient's vascular system. Pieces of plaque material can sometimes dislodge from the stenosis during a balloon angioplasty procedure and become released into the bloodstream. Additionally, while complete vaporization of plaque is the intended goal during a laser angioplasty procedure, particles are not always fully vaporized and may enter the bloodstream.

When any of the above-described procedures are performed for example in the carotid arteries, the release of emboli into the circulatory system can be extremely dangerous to the patient. Debris that is carried by the bloodstream to distal vessels of the brain may cause these cerebral vessels to occlude, resulting in a stroke, and in some cases, death. Therefore, although carotid percutaneous transluminal angioplasty has been performed in the past, the number of procedures performed has been limited due to the justifiable fear of causing an embolic stroke should embolic debris enter the bloodstream and block vital downstream blood passages.

Medical devices have been developed to attempt to deal with the problem created when debris or fragments enter the circulatory system following treatment utilizing any one of the above-identified procedures. One approach which has been attempted is the cutting of any debris into minute sizes which pose little chance of becoming occluded in major vessels within the patient's vasculature. However, it is often difficult to control the size of the fragments which are formed, and the potential risk of vessel occlusion still exists, making such procedures in the carotid arteries a high-risk proposition.

Other techniques which have been developed to address the problem of removing embolic debris include the use of catheters with a vacuum source which provides temporary suction to remove embolic debris from the bloodstream. However, as mentioned above, there have been complications with such systems since the vacuum catheter may not always remove all of the embolic material from the bloodstream, and a powerful suction could cause problems to the patient's vasculature.

Further techniques which have had some limited success include the placement of an embolic protection device such as a filter or trap downstream from the treatment site to capture embolic debris before it reaches the smaller blood vessels downstream. Such embolic protection devices enable the filtering of embolic debris which may be released into the bloodstream during the treatment to the vessel, and yet allow a sufficient amount of oxygenated blood to flow past the device to supply vital organs downstream from the treatment site.

However, there have been problems associated with embolic protection devices, particularly during the assembly, insertion, and deployment thereof. The device may be mounted on the guide wire in an inconvenient manner so as to be fixedly secured thereto. Also, the mounting of the device on the guide wire, such that the device is affixed to and rotatable with the guide wire, may result in the entangling of the device in a delivery sheath, upon the device being directed in the delivery sheath through the patient's anatomy to the position distal to the interventional procedure site. Further, the expansion and deployment of the embolic protection device may not result in full and complete expansion thereof, and consequently may not seal off the inner wall of the blood vessel about the entire circumference thereof, which can result in embolic material bypassing the device. The guiding, tracking, positioning and deployment of the embolic protection device in the patient's vasculature and at the location distal to the interventional procedure site for embolic protection can be difficult and formidable.

Therefore, the present invention provides improved systems and methods for treating stenosis in blood vessels which enable an embolic protection device to be efficiently assembled and to effectively navigate through a patient's vasculature for deployment at a location distal to an interventional procedure site. It also enables the device to expand so as to effectively seal off the inner surface of the blood vessel wall, to capture embolic material, and to prevent embolic material from bypassing the embolic protection device. The improved systems and methods of the present invention further enable the efficient positioning of the embolic protection device at the location distal to the interventional procedure site, to enable the effective capture of embolic material. Also, the invention is formed of expandable material in such a manner as to accommodate the effective bending, tracking, and deploying thereof. Moreover, the systems and methods are relatively easy for a physician to use, while enabling the effective delivery and recovery of a filtering system capable of removing embolic debris released into the bloodstream. The inventions disclosed herein satisfy these and other needs.

SUMMARY OF THE INVENTION

The present invention, in general, provides a system and method for enabling the insertion and removal of a filtering system for capturing and retaining embolic debris from a blood vessel. The embolic debris may be created during the performance of a therapeutic interventional procedure, such as a balloon angioplasty or stenting procedure. The filtering system prevents the embolic debris from lodging and blocking blood vessels downstream from the interventional site. The present invention is particularly useful for enabling an interventional procedure to be performed in vital arteries, such as the carotid arteries, in which critical downstream blood vessels can become blocked with embolic debris, including the main blood vessels leading to the brain or other vital organs. As a result, the present invention provides the physician with a higher degree of confidence in the efficient operation of a filtering system for the collection and removal of embolic debris from the blood vessel when performing high-risk interventional procedures.

The present invention enables a filtering system to be deployed in the blood vessel at a location distal to the area of treatment in the interventional procedure site. It also enables the blood to pass therethrough to enable blood to flow past the filter. It further enables the blood to be filtered to capture and retain any embolic debris which may be created during the interventional procedure.

More particularly, for example, in an embodiment of the present invention, a system is provided for enabling the effective assembly thereof for engagement with a guide wire. The present invention also enables the system to expand against the inner surface of a wall of a blood vessel so as to efficiently seal off the inner surface thereof, for enabling the capture of embolic material which may be released into the blood vessel during the therapeutic interventional procedure. Further, the system enables navigation thereof through a patient's blood vessel, including tortuous vasculature, to a position distal to an interventional procedure site, for deployment of the embolic protection device.

The system includes a guide wire, including a distal end, which is positionable within the blood vessel so as to extend to a position distal to an interventional procedure site. The system also includes a filter device, which is snap-fittable so as to engage the distal end of the guide wire, for effective and convenient engagement therewith. Elements of the filter device which enable the filter device to be snap-fitted to the guide wire are comprised of radiopaque material, for providing a reference for positioning the filter device in the patient's vasculature. The filter device is comprised of expandable material, and is formed so that an end thereof is in tension, and another portion is in compression, to aid in the bending of the filter device in tortuous vasculature.

The above objects and advantages of the present invention, as well as others, are described in greater detail in the following description, when taken in conjunction with the accompanying drawings of illustrative embodiments.

BRIEF DESCRIPTION OF THE DRAWINGS

FIG. 3 is a partly cross-sectional view taken along the line 3—3 of FIG. 1.

FIG. 4 is a plan view of a flattened rolled out form of a tube of material for forming the filter device, in the embodiment of the invention.

DETAILED DESCRIPTION OF THE PREFERRED EMBODIMENTS

Figure 1:
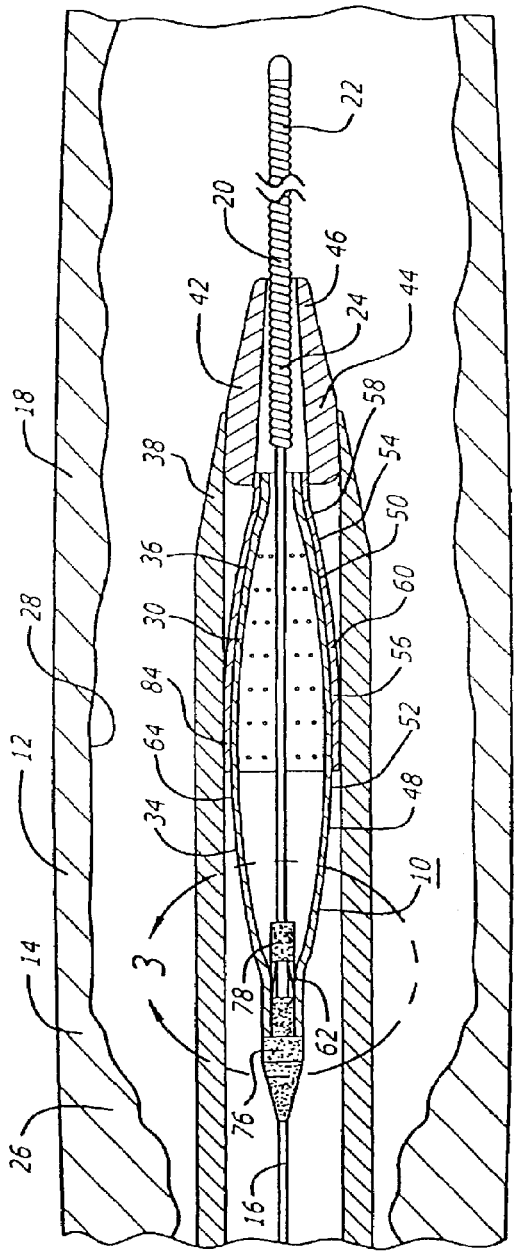
FIG. 1 is an elevational fragmentary partly-sectional view of an embodiment of the present invention, disposed within the internal carotid artery of a patient, including a delivery sheath and an unexpanded filter device.

The present invention is directed to an improved system and method for enabling the capture of embolic material which may be released into the blood vessel during the therapeutic interventional procedure, in an efficient and effective manner. The invention enables a filter device to be snap-fined to a guide wire for effective and convenient engagement therewith, enables rotational movement of the filter device independent of rotational movement of the guide wire, and inhibits translational movement of the filter device along the guide wire. The present invention is further directed to efficiently providing a reference for positioning the filter device in the patient's anatomy. The filter device is also formed of expandable material, and includes an end thereof which is formed so as to be in tension, enabling a portion of the filter device to be in tension and another portion to be in compression, to aid the filter device in the bending thereof in tortuous vasculature.

The embodiments of the improved system and method are illustrated and described herein by way of example only and not by way of limitation. While the present invention is described as applied to the carotid arteries of the patient, those skilled in the art will appreciate that it can also be used in other body lumens as well, such as the coronary arteries, renal arteries, saphenous vein grafts and other peripheral arteries. Additionally, the present invention can be utilized when performing any one of a number of interventional procedures, such as stenting, balloon angioplasty, laser angioplasty or atherectomy.

In the drawings, wherein like reference numerals denote like or corresponding parts throughout the drawing figures, and particularly in the embodiments in accordance with the invention as shown in FIGS. 1–4, for example, a system 10 is provided for enabling an interventional procedure to be performed in a blood vessel 12 at an area of treatment 14. The system 10 is atraumatic, to inhibit injury to the patient. It includes a guide wire 16 which enables the system 10 to be positioned distal to the area of treatment 14. The system 10 is placed within the carotid artery 18 or other blood vessel of the patient, and is guided into position by the guide wire 16. The guide wire 16 includes a tip coil 20 at a distal end 22 thereof. The tip coil includes a proximal end 24. The carotid artery 18 has the area of treatment 14 therein, which comprises the interventional procedure site, wherein atherosclerotic plaque 26 has built up against the inside wall 28, which decreases the diameter of the carotid artery 18. As a result, blood flow is diminished through this area.

The therapeutic interventional procedure comprises implanting an expandable interventional instrument at the interventional procedure site 14, to press the build-up of plaque 26 of the stenosis against the inside wall 28, to increase the diameter of the occluded area 14 of the artery 18, and to help restore sufficient flow of blood to the downstream vessels leading to the brain. The expandable interventional instrument not only helps increase the diameter of the occluded area, but helps prevent restenosis in the area of treatment 14. The interventional instrument is expandable upon deployment thereof at the interventional procedure site 14.

The system 10 of the present invention enables the delivery of a filter device 30 to a location distal to the area of treatment 14, to enable deployment of the filter device 30 at the location distal to the area of treatment 14, and to enable the removal of the filter device 30 from the delivered and deployed position thereof. The filter device 30 filters the blood in the blood vessel 12, so as to pass blood therethrough and capture embolic material 32 which may be released in the blood vessel 12 during the interventional procedure. It engages the distal end 22 of the guide wire 16, so as to enable the filter device 30 to be placed within the carotid artery 18 or other blood vessel of the patient and guided into position distal to the area of treatment 14. The filter device 30 includes a proximal portion 34 and a distal portion 36.

Referring to FIGS. 1–4, in an embodiment pursuant to the present invention, for example, the system 10 enables movement thereof through the patient's blood vessel 12 to a position distal to the area of treatment 14 for deployment of the filter device 30. The system 10 further enables expansion of the filter device 30 against the inside wall 28 of the blood vessel 12 and the sealing off of the inside wall 28, to enable the capture of embolic material 32 which may be released into the blood vessel 12 during the therapeutic interventional procedure.

Figure 2:
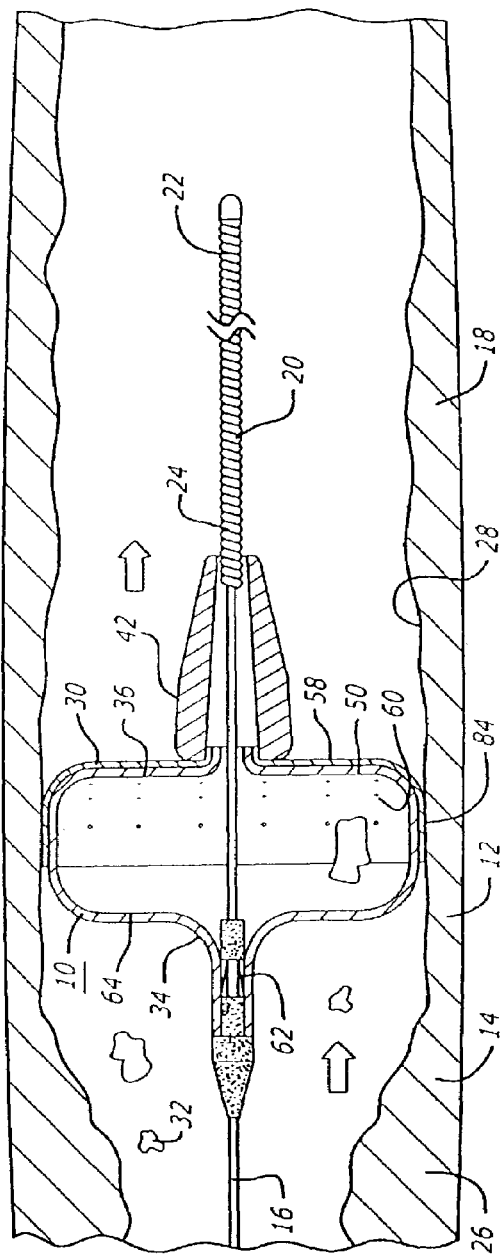
FIG. 2 is a similar view of the embodiment shown in FIG. 1, wherein the delivery sheath has been removed and the filter device has expanded.

As illustrated in FIGS. 1–3, the system 10 in accordance with the embodiment of the invention includes the guide wire 16, positionable within the blood vessel 12, and extendable to a position distal to the interventional procedure site 14.

The system 10 further includes the filter device 30, which is snap-fitted for engagement with the distal end 22 of the guide wire 16. The filter device 30 extends within a delivery sheath 38 for delivery to the interventional procedure site 14. The delivery sheath 38 includes a distal portion 40. The system 10 further includes an obturator 42, which includes a proximal end 44 and a distal end 46. The obturator 42 extends between the delivery sheath 38 and the tip coil 20, such that the distal end 46 of the obturator 42 extends along the proximal end 24 of the tip coil 20, and the proximal end 44 of the obturator 42 is substantially abutted by the distal portion 40 of the delivery sheath 38 when the delivery sheath 38 is extended over the filter device 30. The obturator 42 provides a smooth transition between the delivery sheath 38 and the tip coil 20, so as to slide smoothly around tortuous anatomy in the blood vessel 12, and to inhibit digging into, scraping, or damaging the inside wall 28 of the blood vessel 12 thereby.

The filter device 30 is deployed at the location in the patient's blood vessel 12 distal to the area of treatment 14, upon withdrawal of the delivery sheath 38. It captures embolic material 32 which may be released into the blood in the blood vessel 12 during the interventional procedure. Upon being snap-fitted onto the distal end 22 of the guide wire 16, the filter device 30 engages the guide wire 16, and enables rotation of the filter device 30 independent of rotation of the guide wire 16, while inhibiting translation thereof along the guide wire 16.

A cage 48 is included in the filter device 30. The cage 48 is snap-fitted onto the distal end 22 of the guide wire 16 for engagement therewith, and filter material 50, for filtering embolic material 32, is secured to the cage 48. The cage 48 includes a proximal portion 56 and a distal portion 58, and the filter material 50 includes a proximal end 52, a distal end 54, and a plurality of holes 60 therein for filtering embolic material 32. The proximal end 56 of the filter material 50 is secured to the cage 48, and the proximal end 44 of the obturator 42 extends over the distal portion 58 of the filter material 50.

The cage 48 further includes an engaging element 62, located at the proximal portion 52 thereof, as shown in enlarged view in FIG. 3, for enabling the cage 48 to snap-fit so as to engage the distal end 22 of the guide wire 16. The engaging element 62 enables the cage 48 to be snap-fitted onto the distal end 22 of the guide wire 16. The cage 48, upon being snap-fitted onto the distal end 22 of the guide wire 16, enables rotational movement of the cage 48 independent of rotational movement of the guide wire 16, and inhibits translational movement of the cage 48 along the guide wire 16. The cage 48 further includes a plurality of struts 64.

In the filter device 30, as shown in FIG. 4, the plurality of struts 64 of the cage 48 comprise a plurality of proximal ribs 66, a plurality of distal ribs 68, and a ring 70, which extends intermediate the plurality of proximal ribs 66 and the plurality of distal ribs 68. The ring 70, for example, includes a plurality of segments 72 and 74, and each adjacent pair of the plurality of segments 72 and 74 is expandable to form a generally v-shaped section of the ring 70, to seal off the inside all 28 of the blood vessel 12, so as to inhibit the formation of a gap between the cage 48 and the blood vessel inside wall 18 through which embolic material 32 may otherwise flow.

As seen in FIGS. 1–3, the system 10 further includes a proximal stop 76 and a distal stop 78, to be secured to the distal end 22 of the guide wire 16, and having a space 80 between the proximal stop 76 and the distal stop 78. The proximal stop 76 and the distal stop 78 comprise a pair of bushings, which are comprised of radiopaque material, to provide a reference for the operator of the system 10 to position the filter device 30 in the patient's blood vessel 12. The engaging element 62 of the cage 48 enables the cage 48 to be snap-fined to the proximal stop 76 and the distal stop 78 in the space 80 therebetween. The engaging element 62 includes at least one tab 82, which is pre-bent inwardly, for example, for flexing and engaging the proximal stop 76 and the distal stop 78 in the space 80 between the proximal stop 76 and the distal stop 78. The inner diameter of the filter device 30 is at least slightly larger than the outer diameter of the tip coil 20, enabling the filter device 30 to be snap-fined from the distal end 22 of the guide wire 16. The inner diameter of the tabs 82, for example, are at least slightly larger than the outer diameter of the distal stop 78, for enabling the filter device 30 to slide thereover, and the tabs 82 to snap-fit into position in the space 80 so as to bear against the distal stop 78. Alternatively, for example, the locations of the proximal stop 76 and the distal stop 78 could be reversed, whereby the cage 48 may be snap-fined from a proximal end of the guide wire 16. The snap-fined engaging element 62 inhibits translational movement of the filter device 30 relative to the guide wire 16, while enabling rotational movement of the filter device 30 independent of rotational movement of the guide wire 16.

The cage 48 of the filter device 30, as depicted in FIG. 4, may be formed from a hypotube 84 of expandable material. The hypotube 84 includes a pair of ends 86 and 88. The system 10 further includes a spring 90, connected to the end 86 of the hypotube 84, such that a portion of the cage 48 formed by the hypotube 84 is in tension, and another portion is in compression, to aid the cage 48 in the bending thereof in tortuous vasculature. The tabs 82 are formed at the end 86 of the hypotube 84 to which the spring 90 is connected.

Referring to FIGS. 1–4, in a method for the use of the embodiment in accordance with the present invention, for example, the system 10 enables movement thereof through the patient's blood vessel 12 to the location distal to the area of treatment 14 for deployment of the filter device 30, and seals off the inside wall 28 of the blood vessel 12 to enable the capture of embolic material 32. The filter device 30 and the obturator 42 are assembled, and the proximal stop 76 and the distal stop 78, which comprise a pair of bushings, are mounted on the guide wire with the space 80 therebetween. The inner diameter of the filter device 30, for example, is at least slightly larger than the outer diameter of the tip coil 20, and the at least one tab 82 is pivotable, so as to enable the filter device 30 to be inserted over the tip coil 20. The assembly of the filter device 30 and the obturator 42, for example, is inserted over the tip coil 20 to the position where the tabs 82 snap-fit into the space 80 between the pair of bushings comprising the proximal stop 76 and the distal stop 78 mounted on the guide wire 16, so as to snap-fit the filter device 30 to the distal end 22 of the guide wire 16, for efficient engagement therewith. The delivery sheath 38 is extended over the guide wire 16 so as to enclose the filter device 30 therein, and such that the distal portion 40 of the delivery sheath 38 substantially abuts the proximal end 44 of the obturator 42.

The system 10 is positioned in the patient's vasculature 12 utilizing any one of a number of different methods. In one preferred method of positioning the system 10, the delivery sheath 38, with the filter device 30 therein, is inserted into and extended through the patient's vasculature 12, to cross the stenosis in the blood vessel 12, so as to extend to a position distal to the interventional procedure site 14. The radiopaque proximal stop 76 and distal stop 78 of the engaging element 62 provide a reference for enabling the operator to accurately position the filter device 30 in the patient's vasculature 12. As seen in FIG. 4, the spring 90, connected to the end 86 of the hypotube 84 of expandable material at which the tabs 82 are formed, causes such portion of the cage 48 formed by the hypotube 84 to be in tension, and another portion to be in compression, aiding the cage 48 in the bending thereof in tortuous vasculature.

The guide wire 16 is rotatable during insertion thereof through the patient's vasculature 12, to enable guiding and directing thereof. The snap-fitted filter device 30 is rotatable on the guide wire 16 independent of rotation of the guide wire 16, during insertion of the filter device 30 through the patient's anatomy 12, to inhibit entanglement thereof, while the filter device 30 is also inhibited from translational movement thereof. The delivery sheath 38 is then withdrawn, enabling the filter device 30 to deploy so as to capture embolic material 32 which may be released in the blood vessel 12 during the interventional procedure.

After the delivery sheath 38 is withdrawn, the filter device 30, snap-fitted to the guide wire 16 at the proximal portion 52 of the cage 48 such that the tabs 82 extend between the proximal stop 76 and the distal stop 78, is released from being enclosed in the delivery sheath 38. The filter device 30 then expands and bears against the inside wall 28 of the blood vessel 12. The expansion of the filter device 30 so as to press against the inside wall 28 of the blood vessel 12 seals off the inside wall 28 of the blood vessel 12, and inhibits the formation of a gap between the filter device 30 and the blood vessel wall 28, through which embolic material 32 may otherwise flow. The filter material 50 expands with the flow of blood in the blood vessel 12 therethrough, to capture embolic material 32 which may be released during the interventional procedure.

In accordance with the present invention, the particular embodiments set forth above of the system 10 for filtering embolic material are capable of being positioned in a blood vessel. However, other forms of the system 10 may be utilized with the present invention without departing from the spirit and scope of the invention. For example, the system 10 may be comprised of other forms of material. Additionally, while the system 10 is shown as in various shapes in the embodiments herein, it can be formed in any one of a number of different shapes depending upon the construction desired.

Further, the various components may be joined by suitable adhesives such as acrylonitrile based adhesives or cyanoacrylate based adhesives. Heat shrinking or heat bonding may also be employed where appropriate. Plastic-to-plastic or plastic-to-metal joints can be effected by a suitable acrylonitrile or cyanoacrylate adhesive. Variations can be made in the composition of the materials to vary properties as needed. Based on the present disclosure, other adhesives and applications are known to one skilled in the art.

In view of the above, it is apparent that the system and method of the embodiment of the present invention enhances substantially the effectiveness of performing interventional procedures by providing a filter device for filtering embolic material, to be snap-fined for engagement with a guide wire, and independently rotatable relative to the guide wire, for efficient assembly, insertion and removal thereof. The system and method further enable the filter device to expand against the inner wall of a blood vessel so as to seal off the inner surface thereof, to inhibit gap formation and the passing of embolic material therethrough. The system and method also include a pair of radiopaque bushings for enabling snap-fining engagement of the filter device with the guide wire, which provide references for the positioning of the filter device in the patient's vasculature. The filter device of the system and method is formed of expandable material including a portion thereof in tension, and another portion in compression, for aiding the filter device in bending thereof in tortuous vasculature.

While the present invention has been described in connection with the specific embodiments identified herein, it will be apparent to those skilled in the art that many alternatives, modifications and variations are possible in light of the above description. Accordingly, the invention is intended to embrace all such alternatives, modifications and variations as may fall within the spirit and scope of the invention disclosed herein.

What is claimed:

1. A system for enabling the capture of embolic material which may be released into a blood vessel during a therapeutic interventional procedure, comprising:
   a guide wire, including a distal end, adapted to be positioned within the blood vessel and to extend to a position distal to an interventional procedure site, the guide wire including a proximal stop and a distal stop, adapted to be secured to the distal end of the guide wire, and having a space between the proximal stop and the distal stop; and
   a filter device, adapted to be positioned and deployed at a location in the patient's vasculature distal to the interventional procedure site, and to capture embolic material which may be released into the blood in the blood vessel during the interventional procedure, including an engaging element, for enabling the filter device to be snap-fitted so as to engage the distal end of the guide wire;
   wherein the engaging element of the filter device includes a snap-fitting component and is adapted to enable snap-fitting engagement within the space formed between the proximal stop and distal stop.

2. The system of claim 1, wherein the filter device, upon being snap-fitted to the distal end of the guide wire, is adapted to enable rotational movement of the filter device independent of rotational movement of the guide wire.

3. The system of claim 2, wherein the filter device, upon being snap-fitted to the distal end of the guide wire, is adapted to inhibit translational movement of the filter device relative to the guide wire.

4. The system of claim 1, wherein the proximal stop and a distal stop are made from radiopaque material for providing a reference for positioning the filter device in the patient's vasculature.

5. The system of claim 1, wherein the filter device includes a cage, adapted to be engaged with the distal end of the guide wire, and filter material, for filtering embolic material, secured to the cage.

6. The system of claim 5, wherein the cage includes a plurality of struts.

7. The system of claim 5, wherein the cage includes a proximal end, and the engaging element is located at the proximal end of the cage.

8. The system of claim 7, wherein the cage includes a distal end, the obturator further includes a proximal portion, and the proximal portion of the obturator is adapted to extend over the distal portion of the cage.

9. The system of claim 1, wherein the guide wire includes a tip coil, at the distal end of the guide wire, the tip coil includes a proximal portion, and the system further comprises an obturator, which includes a distal portion, wherein the distal portion of the obturator is adapted to extend over the proximal portion of the tip coil.

10. The system of claim 1, wherein the filter device is adapted to be formed from a hypotube of expandable material.

11. The system of claim 10, wherein the hypotube includes a plurality of ends, and the system further comprises a spring, adapted to be connected to an end of the hypotube, to enable a portion of the cage, to be formed from the hypotube by the system, to be in tension, so as to aid in the tracking and deploying of the cage in tortuous vasculature.

12. The system of claim 11, wherein the hypotube includes at least one tab, formed at the end thereof at which the spring is adapted to be connected and which is adapted to be in tension.

13. The system of claim 1, wherein the proximal stop and the distal stop comprise a pair of bushings.

14. The system of claim 1, wherein the filter device includes a cage, adapted to be snap-fitted onto the distal end of the guide wire, and filter material, for filtering embolic material, and the filter material includes a proximal end, secured to the cage, and a distal portion, and the proximal portion of the obturator extends over the distal portion of the filter material.

15. A system for enabling the capture of embolic material which may be released into a blood vessel during a therapeutic interventional procedure, comprising:
   a guide wire, including a distal end, adapted to be positioned within the blood vessel and to extend to a position distal to an interventional procedure site, the guide wire including a proximal stop and a distal stop, adapted to be secured to the distal end of the guide wire, and having a space between the proximal stop and the distal stop; and
   a filter device, adapted to be positioned and deployed at a location in the patient's vasculature distal to the interventional procedure site, and to capture embolic material which may be released into the blood in the blood vessel during the interventional procedure, including an engaging element, for enabling the filter device to be snap-fitted so as to engage the distal end of the guide wire;
   wherein the engaging element of the filter device is adapted to enable engagement within the space formed between the proximal stop and distal stop and the engaging element of the filter device comprises at least one tab, adapted to engage the proximal stop and the distal stop in the space between the proximal stop and the distal stop.

16. A method of enabling the capture of embolic material which may be released into a blood vessel during a therapeutic interventional procedure using a system which includes a guide wire having a distal end and a proximal stop, a distal stop and a space formed between therebetween, adapted to be positioned within the blood vessel, and a filter device adapted to be positioned and deployed at a location in the patient's vasculature distal to the interventional procedure site to capture embolic material, including an engaging element including a snap-fitting component, for enabling the filter device to be snap-fitted so as to engage the distal end of the guide wire, wherein the method comprises:

snap-fitting the filter device so as to engage the space created between the proximal stop and the distal stop of the guide wire;

inserting the filter device and the guide wire to the location in the patient's vasculature distal to the interventional procedure site; and expanding the filter device for deployment thereof.

17. The method of claim 16, wherein the engaging element of the filter device is adapted to allow enable the filter device to rotate on the guide wire.

18. The method of claim 16, wherein the engaging element, upon being snap-fitted to the distal end of the guide wire, is adapted to inhibit translational movement of the filter device relative to the guide wire.

19. A method of enabling the capture of embolic material which may be released into a blood vessel during a therapeutic interventional procedure using a system which includes a guide wire having a distal end and a proximal stop, a distal stop and a space formed between therebetween, adapted to be positioned within the blood vessel, and a filter device adapted to be positioned and deployed at a location in the patient's vasculature distal to the interventional procedure site to capture embolic material, including an engaging element, for enabling the filter device to be snap-fitted so as to engage the distal end of the guide wire, wherein the method comprises:

snap-fitting the filter device so as to engage the space created between the proximal stop and the distal stop of the guide wire;

inserting the filter device and the guide wire to the location in the patient's vasculature distal to the interventional procedure site; and expanding the filter device for deployment thereof;

wherein the engaging element of the filter device comprises at least one tab, and wherein snap-fitting comprises engaging the at least one tab in the space between the proximal stop and the distal stop.

* * * * *

UNITED STATES PATENT AND TRADEMARK OFFICE
CERTIFICATE OF CORRECTION

PATENT NO. : 7,244,267 B2
APPLICATION NO. : 10/465332
DATED : July 17, 2007
INVENTOR(S) : Benjamin C. Huter et al.

It is certified that error appears in the above-identified patent and that said Letters Patent is hereby corrected as shown below:

Title Page, item (56): U.S. PATENT DOCUMENTS, delete "6,635,070 B2 11/2002 Evans et al." and insert --6,635,070 B2 10/2003 Leeflang et al.--.

Title Page, item (56): U.S. PATENT DOCUMENTS, insert --2002/120287 8/2002 Huter--.

Title Page, item (56): U.S. PATENT DOCUMENTS, delete "2003/0015203 A1 1/2003 Roth et al." and insert --2003/0015206 A1 1/2003 Roth et al.--.

Title Page, item (56): U.S. PATENT DOCUMENTS, delete "2003/0078614 A1 4/2003 Sataheih et al." and insert --2003/0078614 A1 4/2003 Salahieh et al.--.

Title Page, item (56): U.S. PATENT DOCUMENTS, delete "2003/0171770 A1 9/2003 Anderson et al." and insert --2003/0171770 A1 9/2003 Kusleika et al.--.

Title Page, item (56): U.S. PATENT DOCUMENTS, after 2005/0203567 A1 9/2005 Linder insert --et al.--.

Title Page, item (56): U.S. PATENT DOCUMENTS, after 2006/0004405 A1 1/2006 Salaeih insert --et al.--.

Column 7,
Line 25, delete "snap-fined" and insert --snap-fitted--.
Line 32, delete "snap-fined" and insert --snap-fitted--.
Line 40, delete "snap-fined" and insert --snap-fitted--.
Line 41, delete "snap-fined" and insert --snap-fitted--.

UNITED STATES PATENT AND TRADEMARK OFFICE
CERTIFICATE OF CORRECTION

PATENT NO. : 7,244,267 B2
APPLICATION NO. : 10/465332
DATED : July 17, 2007
INVENTOR(S) : Benjamin C. Huter et al.

It is certified that error appears in the above-identified patent and that said Letters Patent is hereby corrected as shown below:

Column 9,
Line 12, delete "snap-fined" and insert --snap-fitted--.
Line 20, delete "snap-fining" and insert --snap-fitting--.

Signed and Sealed this

Twenty-fourth Day of June, 2008

JON W. DUDAS
*Director of the United States Patent and Trademark Office*